United States Patent
Banerjee (10) Patent No.: US 6,307,630 B1
(45) Date of Patent: Oct. 23, 2001

(54) TURBIDIMETER ARRAY SYSTEM

(75) Inventor: Ashim K. Banerjee, Westminster, CO (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 09/444,061

(22) Filed: Nov. 19, 1999

(51) Int. Cl.$^7$ .................................................. G01N 21/00
(52) U.S. Cl. ............................................ 356/436; 356/339
(58) Field of Search ..................................... 356/335, 336, 356/337–343, 436, 440, 432; 250/574, 576

(56) References Cited

U.S. PATENT DOCUMENTS

| | | | |
|---|---|---|---|
| 4,534,651 | * 8/1985 | Minikane | 356/440 |
| 4,549,809 | * 10/1985 | Minekane et al. | 356/436 |
| 4,639,137 | * 1/1987 | Hazan et al. | 356/339 |
| 4,826,319 | * 5/1989 | Namba et al. | 356/339 |
| 4,888,484 | * 12/1989 | Harvey | 356/436 |
| 6,134,000 | * 10/2000 | Schmid et al. | 356/246 |

* cited by examiner

Primary Examiner—Hoa Q. Pham
(74) Attorney, Agent, or Firm—Dean P. Edmundson

(57) ABSTRACT

A turbidimeter array system is described in which a common light source and a common detector are used in conjunction with a plurality of test sample chambers for measuring the turbidity of a sample in each of the numerous chambers sequentially. Many embodiments are described for using a common light source and a common detector. The system is cost efficient because the most expensive components are shared.

19 Claims, 8 Drawing Sheets

TURBIDIMETER ARRAY SYSTEM

FIELD OF THE INVENTION

This invention relates to turbidimeters and their use in monitoring the turbidity of water (e.g. drinking water). More particularly, this invention relates to the use of a turbidimeter to monitor the effluent from membrane filters.

BACKGROUND OF THE INVENTION

Many water plants which are used to produce drinking water utilize membrane filters (e.g. micro-filtration, ultra-filtration, and nano-filtration). Typical ultra-filtration membranes have an effective pore size of less than 0.1 micron which means that not only do they completely remove most bacteriological pathogens, but they also have the capability to filter out most viruses. The California Department of Health and other state and federal agencies are considering means by which they can offer virus removal credit to water plants which adopt ultra-filtration technology. If adopted, water plants will be able to save very significant amounts of money by avoiding the costs associated with chemical disinfection of drinking water.

A serious disadvantage associated with the use of filtration membranes is the periodic failure or rupture of a membrane. Typically there are thousands of relatively small diameter elongated membrane fibers contained in a parallel arrangement in a single cartridge, with numerous cartridges (e.g. 1000 or more in racks of 20 to 50) being used simultaneously in a single water plant. Presently, the operator of the plant periodically (e.g. every four hours or so) takes each rack off-line and passes air through one end while the other end is submerged in water. Below a certain air pressure, air should not be able to pass through a membrane, unless the membrane has been punctured or has ruptured. If the membrane has ruptured or been punctured, a stream of bubbles will be detected from that membrane at the submerged end. The failed membrane can then be identified and mechanically plugged, after which the cartridge can be put back into service. The main problem with this approach is that it allows for a four to six hour period during which undesirable material could pass through the cartridge and enter into the effluent water.

Although manufacturers have provided turbidimeters and particle counters for on-line monitoring of water quality, those instruments generally lack sensitivity to sub-micron particles. Furthermore, a full scale water plant would require several hundred membrane cartridges, and the instrumentation costs for monitoring the effluent of each membrane would be prohibitive.

There has not heretofore been provided a system for accurately and efficiently monitoring the effluent of multiple membranes used for ultra-filtration of water.

SUMMARY OF THE INVENTION

It is an object of this invention to provide a turbidimeter system for efficiently monitoring the effluent of a plurality of membrane cartridges comprising a membrane filtration plant.

It is another object of this invention to provide a turbidimeter system in which a plurality of sample chambers are used.

It is a further object of this invention to provide a turbidimeter system with an array of sample chambers and in which a common light source and a common detector are shared for turbidity testing of separate liquid samples contained in the separate chambers.

To accomplish the foregoing and other objects, the present invention provides a turbidimeter array system comprising a plurality of sample chambers for containing a liquid sample to be tested, and wherein the system includes a common light source and a common detector means. In other words, the system includes a plurality of sample chambers which share a common light source and a common detector when a turbidity measurement is made of the liquid in a particular chamber.

In one embodiment, a single light source is adapted to sequentially direct a light beam into each of the sample chambers, and the detector means is adapted to detect light which is scattered by the liquid sample in each of the sample chambers. In another embodiment, a single light source is adapted to direct a light beam to all of the separate sample chambers simultaneously, and a detector is adapted to sequentially detect scattered light from each of the sample chambers. For example, a shutter at each chamber can be moved from a closed position to an open position to allow the light beam to pass into one chamber at a time, and scattered light from that particular chamber is detected by the sole detector. In yet another embodiment, a separate light source is used for each chamber, and a common detector is used to sequentially measure scattered light from the different chambers.

The system of this invention enables efficient monitoring of the turbidity of a plurality of liquid samples contained in a plurality of separate chambers, without requiring a separate light source and separate detector for each sample chamber. Rather, in a preferred embodiment the system utilizes a common light source, detector means, associated control electronics, display, etc.

Other advantages and features of the turbidimeter array system of the invention will be apparent from the following detailed description and the accompanying drawings.

BRIEF DESCRIPTION OF THE DRAWINGS

The present invention is described in more detail hereinafter with reference to the accompanying drawings wherein like reference characters refer to the same parts throughout the several views and in which.

DETAILED DESCRIPTION OF THE INVENTION

Figure 1:
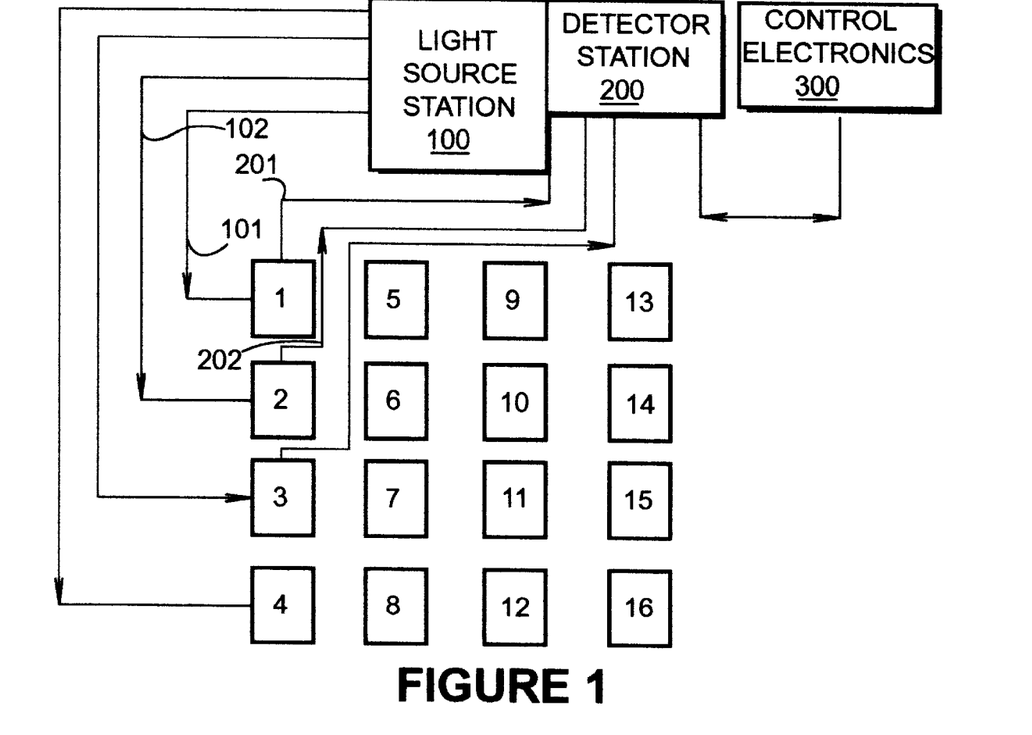
FIG. 1 is a schematic diagram showing an array of 16 separate sample chambers which share a common light source, detector means, and control electronics.

The present invention provides a number of embodiments in which a common light source and a common detector means are shared for turbidity testing of a plurality of liquid samples contained in a plurality of separate chambers or cells. FIG. 1 is a schematic diagram illustrating this concept. There is shown an array comprising 16 separate sample chambers, with one light source station 100, one detector station 200, and one control electronics station 300.

In this embodiment, a separate optical fiber extends between the light source and each of the sample chambers. Also, a separate optical fiber extends between each sample chamber and the detector. The chambers each include appropriate inlet and outlet windows, as required, to enable the light beam to be transmitted into the chamber and to enable scattered light to be transmitted out of the chamber. The chambers preferably each include appropriate inlet and outlet ports for the liquid (e.g. water) which is being tested in each chamber.

When it is desired to test the turbidity of the sample in chamber 1, light from the light source is directed through the optical fiber 101 extending to chamber 1. See also FIG. 2 where the light beam from fiber 101 is shown being transmitted into chamber 1 where it proceeds through the sample. Light which is scattered (e.g. at 90°) by the sample in chamber 1 is transmitted via an optical fiber 201 to the detector station. The conventional control electronics is able to convert the signal generated by the detector into a turbidity value and cause it to be displayed or recorded.

Figure 2:
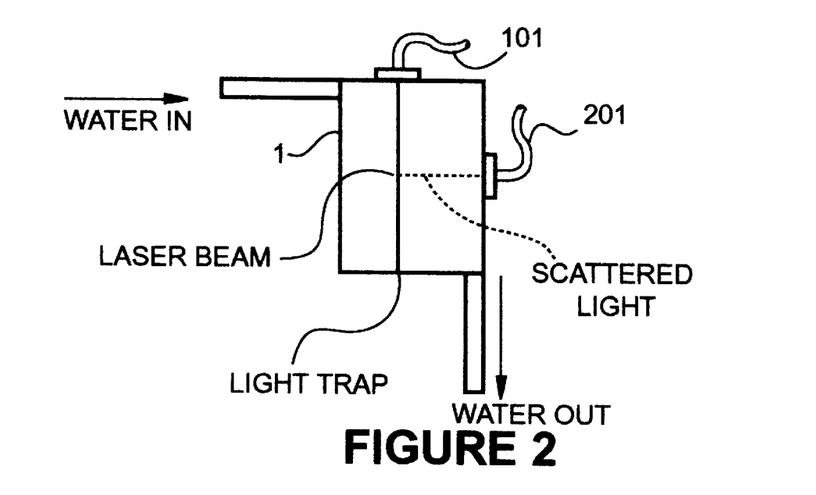
FIG. 2 illustrates one embodiment of a sample chamber of the array shown in FIG. 1.

A similar situation occurs when it is desired to test the turbidity of a sample in chamber 2 using optical fiber 102 to transmit light from the light source 100 and optical fiber 202 to transmit scattered light to the detector. The same technique is used with respect to each of the separate sample chambers. Because each chamber can be tested using the same light source and the same detector and control electronics, the array system is very efficient.

The light source used in this invention may be, for example, a conventional tungsten lamp, or a laser, or even a light emitting diode (LED). Other light sources could also be used, if desired.

The detector means used in this invention may be any conventional light detector such as a photomultiplier tube, photodiode, or avalanche photodiode.

There are a variety of ways to utilize a common light source and common detector in combination with an array of separate sample chambers in accordance with this invention.

Figure 3:
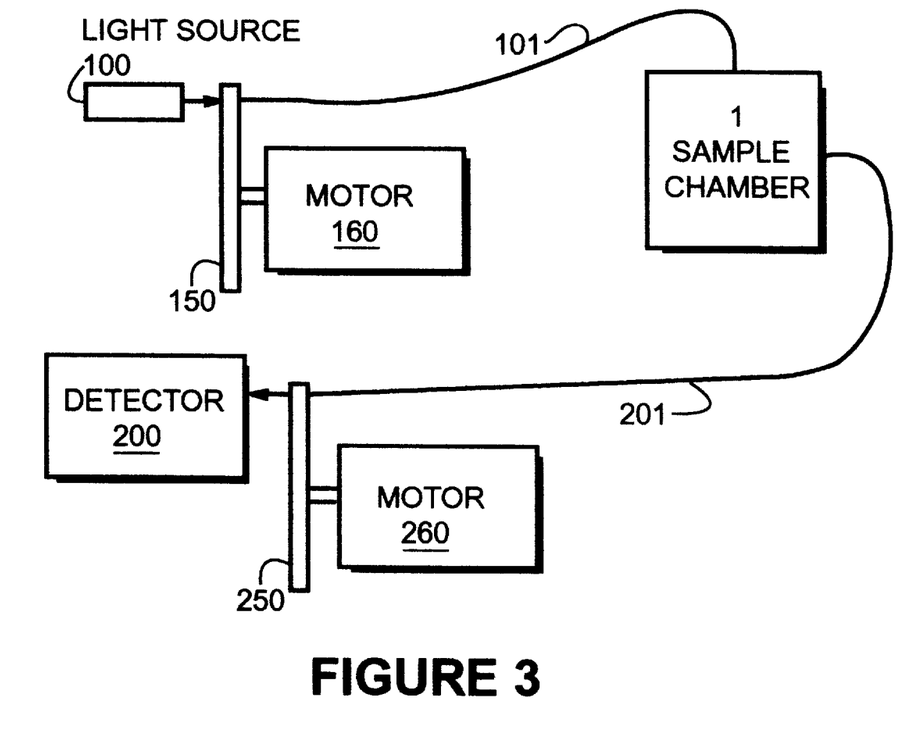
FIG. 3 illustrates one embodiment of the invention in which a first optical fiber transmits light from the light source to a sample chamber, and a second optical fiber transmits scattered light from the sample chamber to a detector means.
Figure 4:
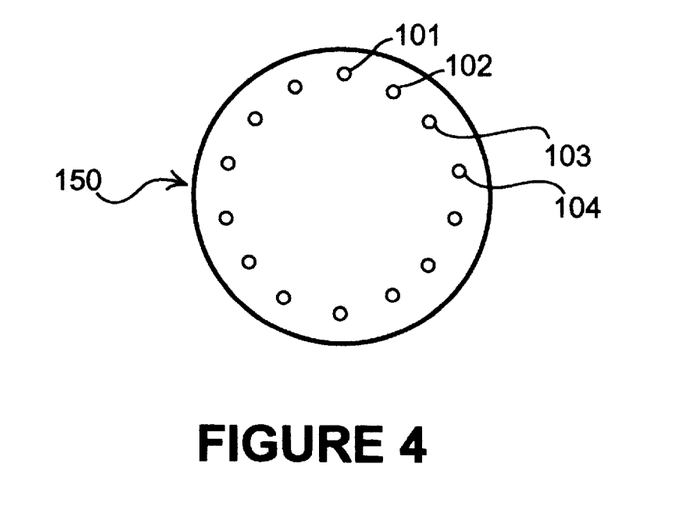
FIG. 4 is a front elevational view of a rotatable disk in which the ends of a set of optical fibers are supported, with each optical fiber being associated with a separate sample chamber.

One of these is illustrated in FIGS. 3 and 4. Each sample chamber has an optical fiber (e.g. 101) which terminates at one end at the chamber inlet window and terminates at its opposite end in rotatable disk 150 adjacent light source 100 (as shown). The rotatable disk 150 can be selectively rotated by means of stepper motor 160 so as to position the end of any desired optical fiber adjacent to the light source.

Each sample chamber also has an optical fiber (e.g. 201) which terminates at one end at the chamber outlet window and terminates at the opposite end in rotatable disk 250 adjacent detector 200. The disk 250 can be rotated by means of stepper motor 260 so as to position the end of the desired fiber 201 adjacent to the detector. When fibers 101 and 201 are adjacent to the light source and the detector, respectively, then the turbidity of the sample in chamber 1 can be determined. Appropriate rotation of disks 150 and 250 enable similar testing of all of the samples in the other chambers in the array. Although only 16 separate chambers are illustrated in FIGS. 1–4, there may be any desired number of separate chambers for separate samples to be tested.

Figure 5:
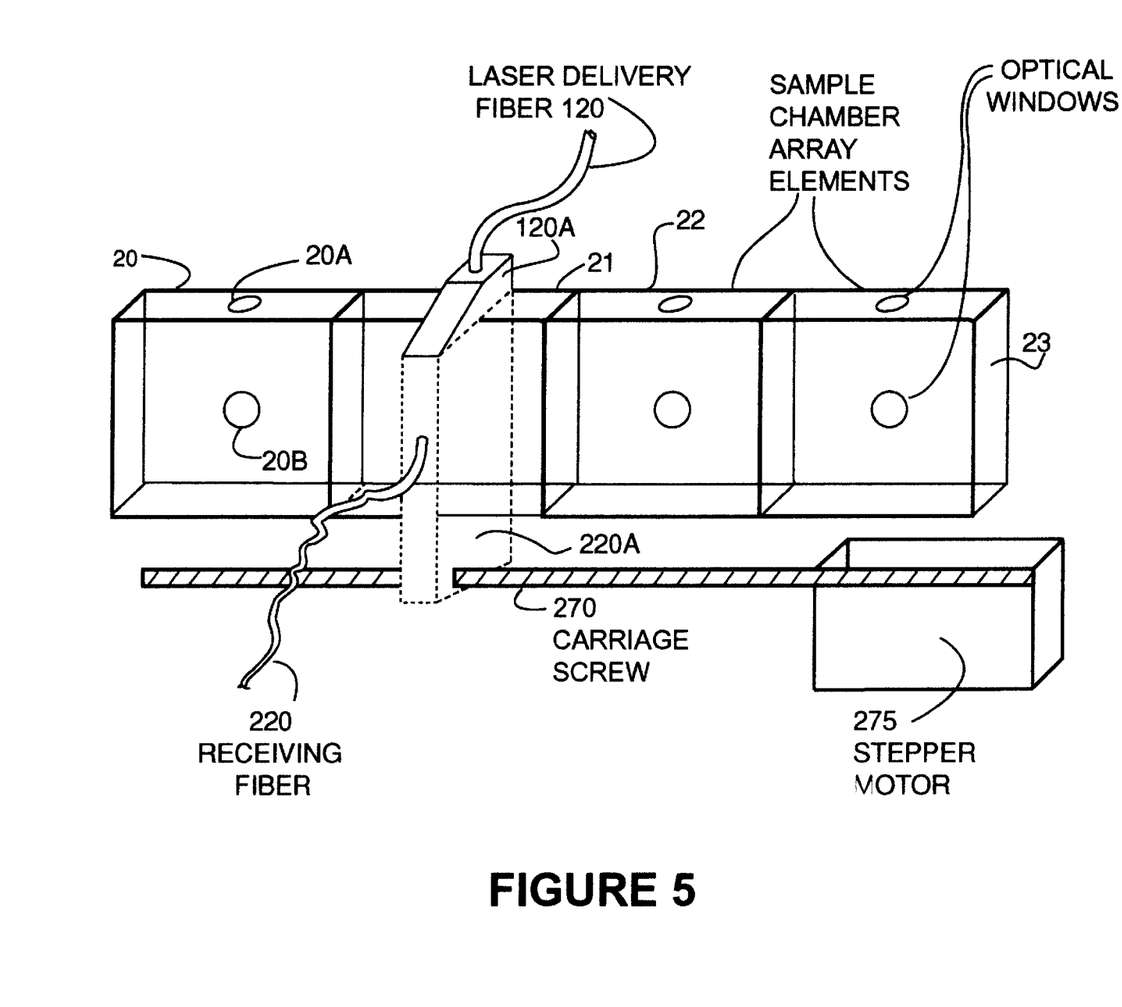
FIG. 5 illustrates another embodiment wherein a common light source and a common detector means are shared when testing samples contained in a plurality of separate chambers.

FIG. 5 illustrates another manner in which a common light source and a common detector may be used for testing turbidity of a plurality of liquid samples in a plurality of separate chambers. Thus, there is shown a plurality of separate chambers 20, 21, 22, 23, etc. Each chamber includes an inlet window 20A, etc. for the light beam from the light source and an outlet window 20B for enabling scattered light to exit the chamber. The light source provides a light beam which is introduced into the chamber by means of an optical fiber 120, and the scattered light is transmitted by optical fiber 220 to a detector. The end of the optical fiber 120 adjacent the sample chamber is supported by block 120A, and the end of the optical fiber 220 adjacent the sample chamber is supported by block 220A. Block 220A is connected to a carriage screw 270 whose rotation is controlled by a stepper motor 275. Block 120A is connected to block 220A, as illustrated, so that they move as a unit. With this arrangement, the light beam fiber and the scattered light fiber are moved simultaneously from one sample chamber to another by the stepper motor. There may be any desired number of separate sample chambers aligned in side-by-side fashion.

Figure 6:
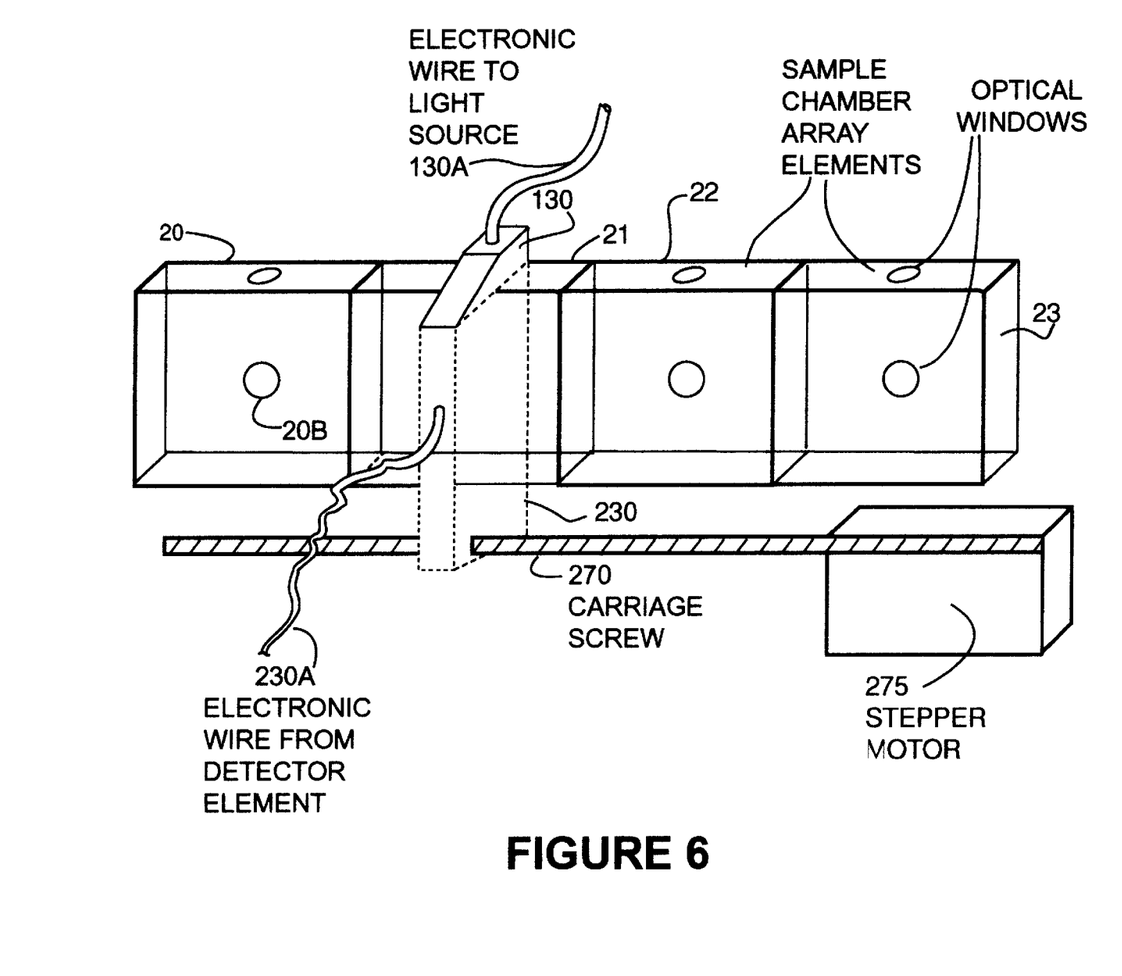
FIG. 6 illustrates yet another embodiment of an array system of the invention wherein a common light source and common detector are shared when testing samples contained in a plurality of separate chambers.

FIG. 6 illustrates another embodiment of a turbidimeter array system of the invention in which a light source 130 (e.g. a laser) and a light detector 230 are secured together and are advanced along a line of sample chambers by the carriage screw 270 and stepper motor 275. A wire 130A provides the electrical energy to drive the laser light source, and wire 230A transmits electrical signals from the light detector to a recorder or a display. In this manner, a common light source and a common detector are used to sequentially test the turbidity of a plurality of separate test samples contained in a plurality of separate chambers.

Figure 7:
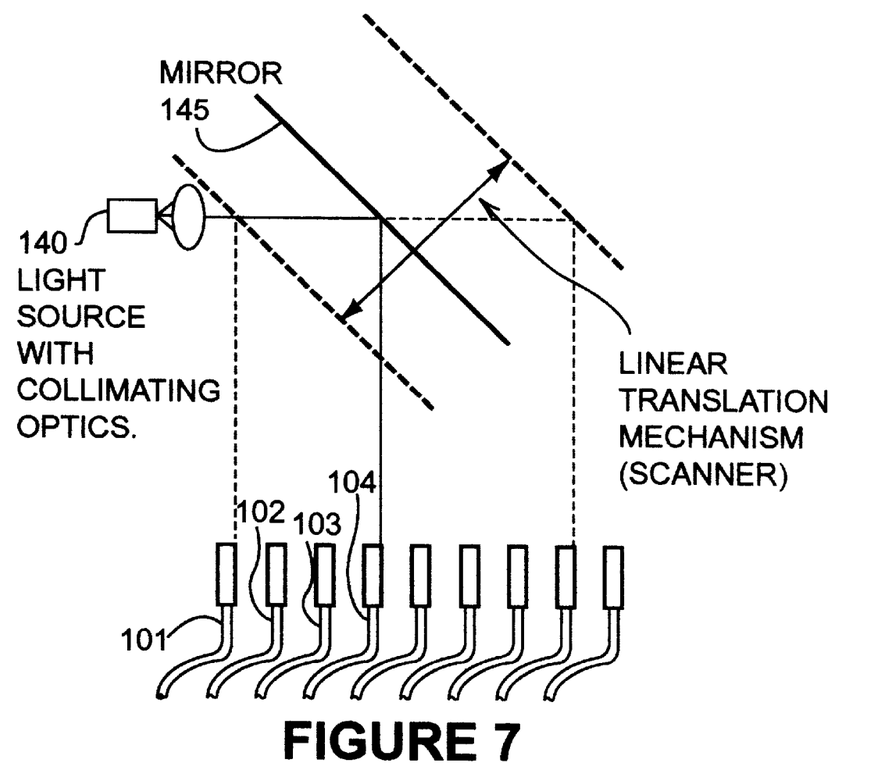
FIG. 7 illustrates another manner in which a common light source may be shared for use by a plurality of separate optical fibers.

FIG. 7 illustrates the use of a single light source 140 and an angled mirror 145 to supply a light beam to any of a plurality of optical fibers 101, 102, etc. which lead to individual sample chambers. In order to direct light from the light source to a particular optical fiber 104, for example, the mirror 145 is moved linearly (e.g. by means of a stepper motor) to the position shown whereby the light beam is reflected directly into the end of optical fiber 104, as shown. By moving the mirror closer to the light source or farther away, the light beam can be reflected into the end of any desired optical fiber.

Figure 8:
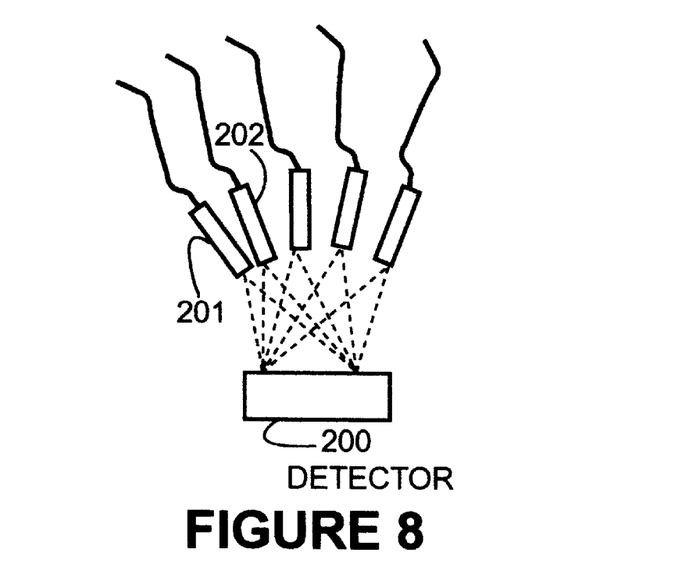
FIG. 8 illustrates another manner in which a common detector may be utilized to receive scattered light from a plurality of separate optical fibers.

FIG. 8 illustrates another embodiment wherein multiple optical fibers 201, 202, etc. transmitting scattered light from a plurality of separate chambers are aimed at a common detector 200. For this embodiment, only one of the optical fibers at a time is permitted to transmit scattered light to the common detector.

Figure 9:
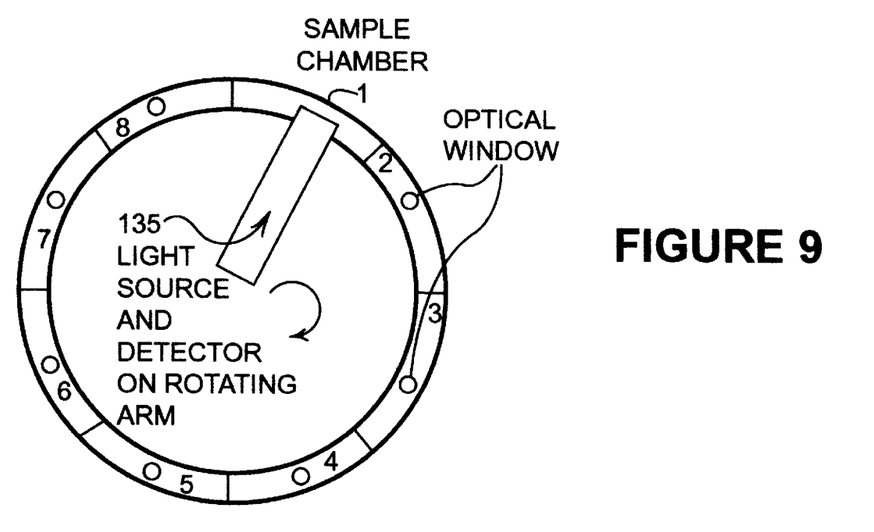
FIG. 9 illustrates another manner in which a common light source and common detector means may be used in conjunction with a plurality of separate sample chambers.

FIG. 9 illustrates a radial arrangement or alignment of a plurality of sample chambers 1 through 8. Each chamber includes an inlet optical window and an outlet optical window. The common light source and common detector are supported on an arm 135 which can be simply rotated in order to be aligned with any desired chamber for testing.

Figure 10:
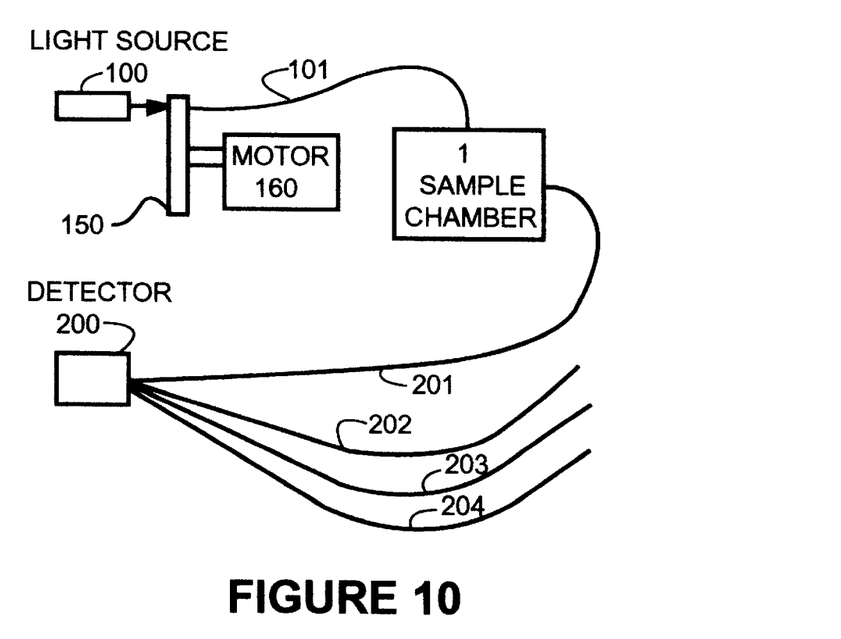
FIGS. 10 and 11 illustrate still further embodiments in which a common light source and a common detector may be used in conjunction with a plurality of separate sample chambers.

FIG. 10 illustrates an embodiment where multiple individual optical fibers 101, etc. are supported at one end in a rotatable disk 150 adjacent the light source 100. Each optical fiber is connected at its opposite end to a respective sample chamber. An optical fiber 201, etc. is connected at one end to the optical outlet window of a respective sample chamber, and the opposite end of each optical fiber terminates at a common detector 200. By rotating disk 150, a light beam is directed to an individual sample chamber, and scattered light from that particular chamber is transmitted directly to the detector. Because only one sample chamber at a time will receive light from the light source, there is no need for multiplexing the several optical fibers for the scattered light. Rather, each of such optical fibers can be connected directly to the detector.

Figure 11:
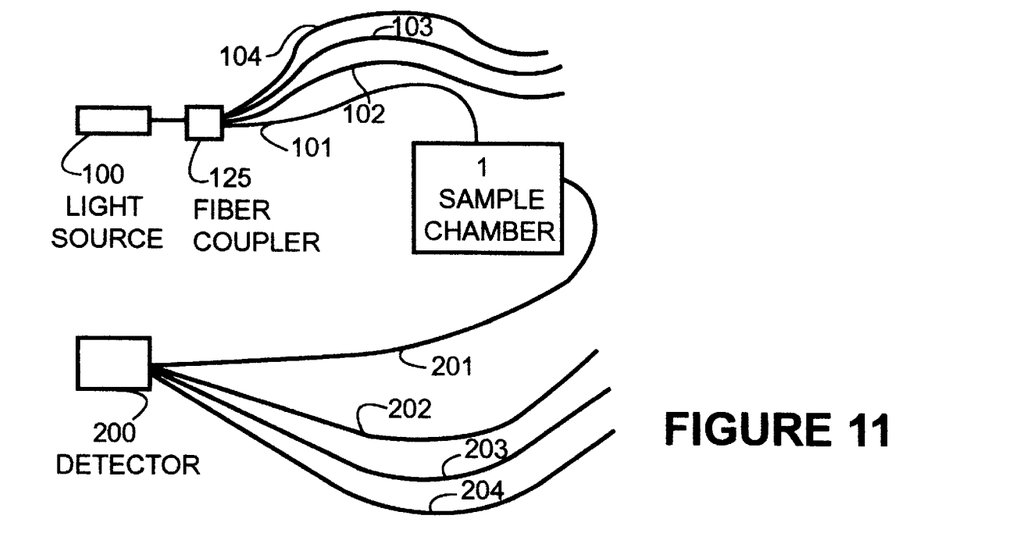

FIG. 11 illustrates yet another embodiment of a turbidimeter array system of the invention in which a common light source 100 and a common detector 200 are used. Light from the light source is directed into fiber coupler 125 in which each end of a plurality of optical fibers 101, 102, etc. are connected. This results in a light beam being transmitted simultaneously through each of the optical fibers. Each optical fiber is connected at its opposite end to a respective sample chamber. Optical fibers 201, 202, etc. are each operatively connected at one end to the optical outlet window of a respective sample chamber, and they are each connected at the opposite end to detector 200. Thus, a light beam is transmitted to all of the sample chambers simultaneously. Each sample chamber can include shutter means for selectively opening or closing the optical inlet window to enable one chamber at a time to receive the transmitted light beam.

Figure 12:
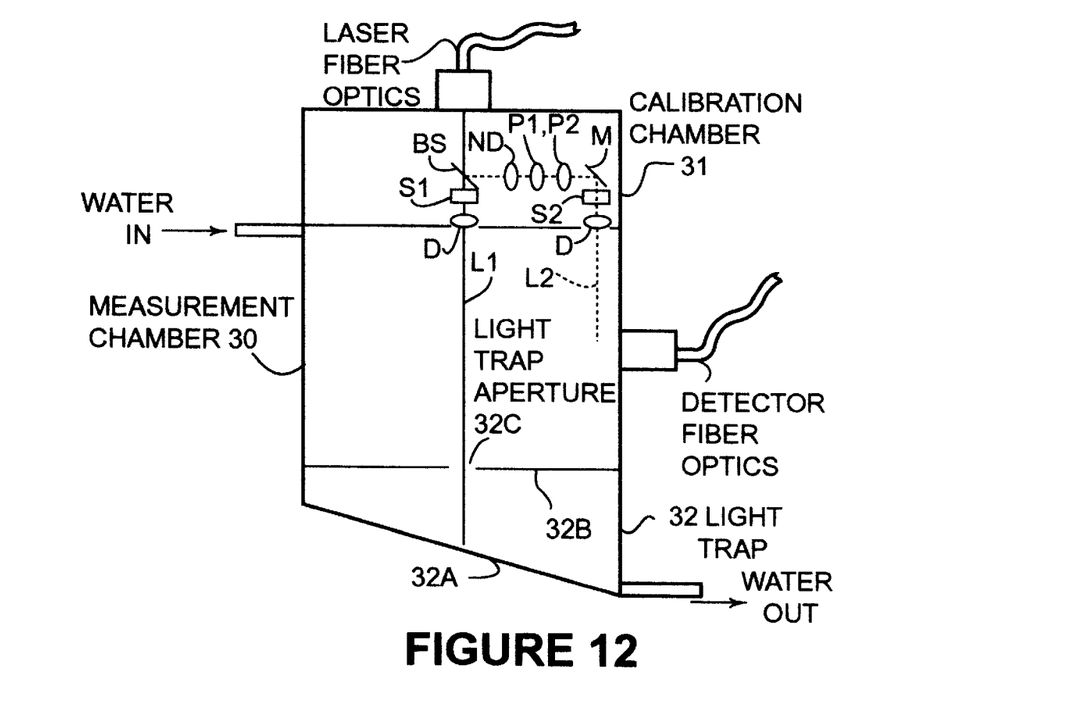
FIG. 12 illustrates the use of a calibration system in the present invention.

FIG. 12 illustrates a sample chamber 30 which is designed to enable verification of the calibration of the unit. The chamber 30 includes a light trap section 32 comprising a sloped or angled floor 32A beneath a horizontal floor 32B in which there is provided an aperture 32C. On top of the measurement chamber 30 there is located a calibration chamber or section 31. The light beam from the light source (e.g. laser fiber optics) first passes through a beam splitter BS which transmits about 90% of the beam and reflects about 10% into the calibration path. The main beam L1 which is transmitted passes through shutter S1, diffuser D, then through the sample in the chamber 30 and through aperture 32C into the light trap 32.

When it is desired to verification the calibration of the unit, shutter S1 is closed and shutter S2 is opened. This enables the light from beam splitter BS to pass through neutral density filter ND (which attenuates the light beam about 1000 times) and two polarizers P1 and P2 to reach mirror M where it is reflected through open shutter S2 and diffuser D and into the sample chamber 30 as beam L2. This calibration beam is factory adjusted using the two polarizers such that it reads as a known amount of turbidity. During verification, the instrument looks for a turbidity reading corresponding to this predetermined value. If the turbidity reading is within preset limits then the instrument is deemed to be functioning properly. If the measured reading is not within the preset limits, then a calibration is performed using the available signal. Alternatively, verification of the calibration can be performed with both shutters S1 and S2 open. In such case, the instrument looks for an increase in the turbidity reading by an amount corresponding to the factory preset calibration signal.

A calibration verification system of the type described above is shown in U.S. Pat. No. 5,912,737, incorporated herein by reference.

Figure 13:
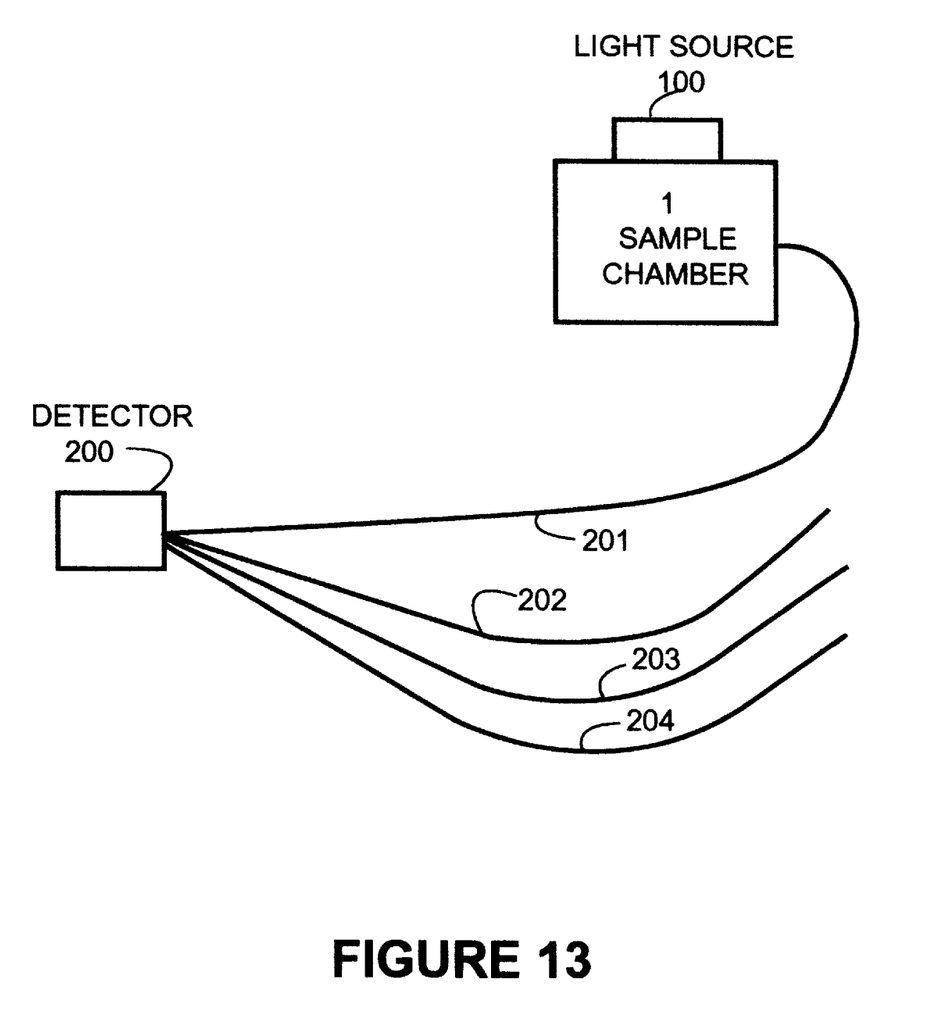
FIG. 13 illustrates another embodiment of the invention in which each sample chamber includes its own light source, and a common detector is used to measure scattered light from the chambers.

FIG. 13 illustrates another embodiment of a turbidimeter array system in which each sample chamber includes its own light source 100 but a common detector 200 is used. An optical fiber 201, 202, 203 204, etc. from each sample chamber extends to the common detector. In this arrangement, only one light source is activated at a time in order to enable a turbidity reading to be taken from a respective sample chamber.

Other variants are possible without departing from the scope and spirit of this invention.

What is claimed is:

1. A turbidimeter array system comprising a plurality of sample chambers each including a liquid sample to be tested, wherein said system includes:

a common light source and a common detector means, wherein said light source directs a light beam into said liquid sample and said detector means detects light scattered by said liquid sample for measuring the turbidity of each of a plurality samples;

calibration verification means operatively associated with each said chamber, wherein said calibration verification means comprises:

(a) a beam splitter for splitting the light from said light source into first and second beams;

(b) polarizer means for polarizing the light in said second beam and controlling the amount of light passing through said polarizer means, and (c) shutter means for controlling transmittance of said second beam into said chamber.

2. A turbidimeter array system comprising:

(a) a plurality of sample chambers each including a liquid sample to be tested;

(b) a single light source means for sequentially directing a light beam into each of said sample chambers;

(c) detector means for sequentially detecting light scattered by said liquid sample in each of said sample chambers and for measuring the turbidity of each of a plurality of liquid samples; and (d) calibration verification means operatively associated with each said chamber, wherein said calibration verification means comprises:

(I) a beam splitter for splitting the light from said light source into first and second beams;

(ii) polarizer means for polarizing the light in said second beam and controlling the amount of light passing through said polarizer means, and (iii) shutter means for controlling transmittance of said second beam into said chamber.

3. A system in accordance with claim 2, wherein each said sample chamber includes a light inlet window and a light outlet window.

4. A system in accordance with claim 3, further comprising first optical fiber means positioned between said light source and said light inlet window for transmitting light to said sample chamber, and further comprising second optical fiber means positioned between said detector means and said light outlet window for transmitting scattered light from said outlet window to said detector means.

5. A system in accordance with claim 4, wherein said first optical fiber means includes a first end positioned at said light inlet window and a second end positioned in a rotatable disk adjacent said light source, wherein rotation of said disk enables said light source to transmit light through a desired one of said first optical fiber means.

6. A system in accordance with claim 4, wherein said second optical fiber means includes a first end positioned at said light outlet window and a second end positioned in a rotatable disk adjacent said detector means, wherein rotation of said disk enables said detector means to detect light transmitted by a desired one of said second optical fiber means.

7. A system in accordance with claim 4, further comprising movable mirror means for reflecting light from said light source selectively into said first optical fiber means.

8. A system in accordance with claim 4, further comprising coupler means for receiving light from said light source and directing the light simultaneously into each said first optical fiber means.

9. A system in accordance with claim 2, wherein said sample chambers are aligned in a side-by-side manner.

10. A system in accordance with claim 9, further comprising carriage means for supporting said light source and said detector means and for advancing the position of said light source and said detector means from one said sample chamber to another of said chambers.

11. A system in accordance with claim 10, wherein said sample chambers are aligned linearly.

12. A system in accordance with claim 10, wherein said sample chambers are aligned radially.

13. A system in accordance with claim 10, wherein said light source comprises a laser.

14. A system in accordance with claim 10, wherein said light source comprises a lamp.

15. A system in accordance with claim 10, wherein said light source comprises a light emitting diode.

16. A system in accordance with claim 2, wherein said detector means comprises a photomultiplier tube.

17. A system in accordance with claim 2, wherein said detector means comprises a photodiode.

18. A system in accordance with claim 2, wherein said detector means comprises an avalanche photodiode.

19. A turbidimeter array system comprising:
 (a) a plurality of sample chambers each including a liquid sample to be tested;
 (b) a light source means operatively associated with each said sample chamber for directing a light beam into said chamber;
 (c) a single detector means for sequentially detecting light scattered by said liquid sample in each of said sample chambers and for measuring the turbidity of each of a plurality of liquid samples; and
 (d) calibration verification means operatively associated with each said chamber, wherein said calibration verification means comprises:
  (I) a beam splitter for splitting the light from said light source into first and second beams;
  (ii) polarizer means for polarizing the light in said second beam and controlling the amount of light passing through said polarizer means, and
  (iii) shutter means for controlling transmittance of said second beam into said chamber.

* * * * *